United States Patent [19]

Luo

[11] Patent Number: 4,620,867
[45] Date of Patent: * Nov. 4, 1986

[54] 1-CARBALKOXYALKYL-3-ARYLOXY-4-(SUBSTITUTED-2'-CARBOXYPHENYL)-AZET-2-ONES AS PLANT GROWTH REGULATORS AND HERBICIDES

[75] Inventor: Tatao Luo, El Sobrante, Calif.

[73] Assignee: Chevron Research Company, San Francisco, Calif.

[*] Notice: The portion of the term of this patent subsequent to Oct. 30, 2001 has been disclaimed.

[21] Appl. No.: 656,068

[22] Filed: Sep. 28, 1984

[51] Int. Cl.$^4$ .............. C07D 205/08; C07D 263/12; C07D 263/14; A01N 43/44
[52] U.S. Cl. .................. 71/88; 548/237; 548/239; 560/35; 540/360
[58] Field of Search .................. 260/239 AL; 71/88

[56] References Cited

U.S. PATENT DOCUMENTS 4,456,467 6/1984 Freenor et al. .............. 260/239 AL
4,479,900 10/1984 Luo .............................. 260/239 AL Primary Examiner—Mark L. Berch
Attorney, Agent, or Firm—S. R. LaPaglia; T. G. DeJonghe; S. L. Biggs

[57] ABSTRACT

Compounds of the formula:

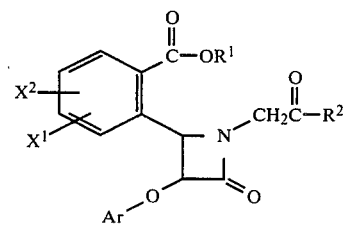

wherein $R^1$ is lower alkyl or benzyl; $R^2$ is lower alkoxy, benzyloxy or the group

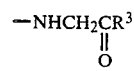

where $R^3$ is lower alkoxy; Ar is phenyl or phenyl substituted with 1 to 3 substituents independently selected from halogen, trihalomethyl, nitro, phenyl, lower alkoxy and lower alkyl; and $X^1$ and $X^2$ are independently hydrogen, halogen, lower alkoxy, or lower alkyl, or $X^1$ and $X^2$ taken together form an aromatic ring fused with the phenyl ring, provided that both $X^1$ and $X^2$ are not hydrogen show activity as plant growth regulators.

33 Claims, No Drawings

1-CARBALKOXYALKYL-3-ARYLOXY-4-(SUB-STITUTED-2'-CARBOXYPHENYL)-AZET-2-ONES AS PLANT GROWTH REGULATORS AND HERBICIDES

BACKGROUND OF THE INVENTION

The present invention relates to 1-carbalkoxyalkyl-3-aryloxy-4-(-substituted-2'-carbalkoxyphenyl)-azet-2-ones activity as plant growth regulators and as herbicides.

The commonly assigned U.S. Pat. No. 4,456,467 of Francis J. Freenor III discloses compounds of the formula:

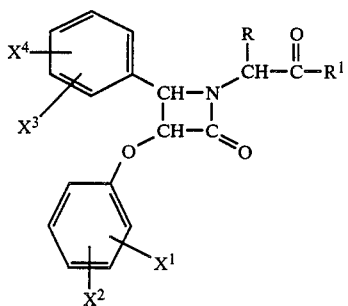

wherein R is hydrogen or alkyl of 1 to 3 carbon atoms; $R^1$ is hydrogen, alkyl of 1 to 6 carbon atoms, alkoxy of 1 to 6 carbon atoms, alkylthio of 1 to 6 carbon atoms or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms, which are active as plant growth regulators.

The commonly assigned U.S. Pat. No. 4,443,372 of Tatao Luo, Louis Russo and Francis J. Freenor III discloses 1-lower alkyl derivatives of 3-aryloxy-4-(2-carbalkoxy)-phenyl-azet-2-one compounds of the formula:

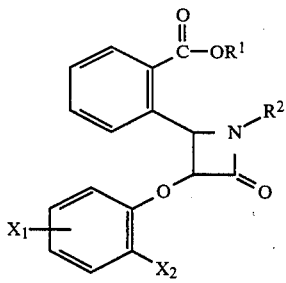

wherein $R_1$ is methyl or ethyl; $R_2$ is lower alkyl; and $X_1$ and $X_2$ are independently hydrogen or halogen which are active as plant growth regulators.

My commonly-assigned U.S. patent application Ser. No. 490,065 now U.S. Pat. No. 4,479,900 discloses compounds of the formula:

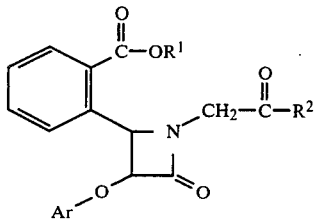

wherein $R^1$ is lower alkyl or benzyl; $R^2$ is lower alkoxy, benzyloxy or the group

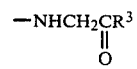

where $R^3$ is lower alkoxy and Ar is phenyl optionally substituted with 1 to 3 substituents independently selected from halogen, trihalomethyl, nitro, and lower alkyl which show plant growth regulating activity.

U.S. Pat. No. 4,181,800 discloses a large group of anti-microbial 2-azetidinone compounds of the general formula:

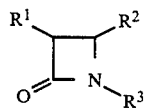

wherein $R^1$ is amino, substituted amino, substituted hydroxy, azido or halogen; $R^2$ is hydrogen, hydroxymethyl, aralkoxyaminomethyl, aryl, aralkenyl, formyl, carboxy, or a residue of a nucleophile; and $R^3$ is a group of the formula:

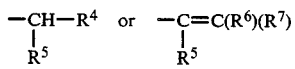

wherein $R^4$ is aryl, aralkyl, arylthioalkyl or a heterocyclic group; $R^5$ is carboxy or its derivative; $R^6$ is alkyl, haloalkyl, arylthio or heterocyclic-thioalkyl; and $R^7$ is hydrogen, haloalkyl or heterocyclic-thioalkyl; (subject to various provisos). The compounds are disclosed as useful antibiotics for treating microbial infections in mammals.

U.S. Pat. No. 4,207,234 discloses a large class of anti-microbial 4-unsubstituted azetidinone compounds which have the general formula:

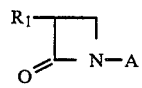

wherein $R_1$ is amino or acylamino; and A is hydrogen or the group:

wherein $R^x$ is hydrogen; $R^y$ is, in pertinent part, hydrogen or alkyl of up to 6 carbon atoms; and $R^2$ is, in pertinent part, carboxy, hydroxy, amino, cyano, or alkyl of up to 6 carbon atoms substituted by carboxy or a salt thereof. These compounds are disclosed as useful as antibiotics to treat microbial infections in mammals.

SUMMARY OF THE INVENTION

The compounds of the present invention are represented by the formula:

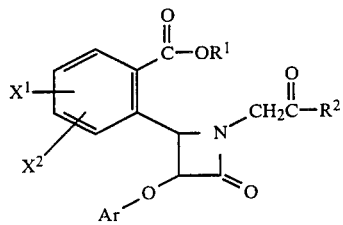

wherein R¹ is lower alkyl or benzyl; R² is lower alkoxy, benzyloxy or the group

wherein R³ is lower alkoxy; Ar is phenyl or phenyl substituted with 1 to 3 substituents independently selected from halogen, trihalomethyl, nitro, phenyl, lower alkoxy and lower alkyl; and X¹ and X² are independently hydrogen, halogen, lower alkoxy, or lower alkyl, or X¹ and X² taken together form an aromatic ring fused with the phenyl ring, provided that both X¹ and X² are not hydrogen.

Among other factors, the present invention is based on my finding that these compounds show surprising activity as plant growth regulators. In particular, these compounds exhibit a significantly higher level of activity than other structurally related compounds. In particular treatment of plants with the compounds of my invention may result in a saving of labor in the case of the plants, such as by decreasing the need for mowing turf or for physical pruning of fruit trees and ornamentals due to the compounds' herbistatic and chemical pruning activities. These compounds may also increase the yield in plants such as cucumbers by increasing both flowering and the proportion of female flowers. The plant growth regulating (PGR) activities of these compounds appear to be very susceptible to structural change, such that while the compounds of this invention having a carbalkoxy group in the ortho position on the 4-phenyl group show unexpectedly good PGR activity, corresponding compounds lacking that group in that position or having other groups in the ortho-position show significantly less PGR activity. It is believed that the trans isomer of these compounds, that is, where the 3-phenoxy and the 4-phenyl groups are in the trans position, has greater PGR activity than the corresponding cis isomer.

As is apparent, the compounds have asymmetric carbon atoms and thus can exist as optical and geometric isomers. Accordingly, the respective optical isomers and geometric isomers, as well as mixtures thereof, are encompassed within the invention.

Preferred X¹ and X² groups include methyl, methoxy, chloro, fluoro and the like.

Preferred R¹ groups include methyl and ethyl.

Preferred R² groups include methoxy, ethoxy and the group

where R³ is lower alkoxy.

Preferred Ar groups include phenyl groups optionally substituted with up to two halogen atoms. Especially preferred Ar groups are phenyl groups having a halogen atom in the para position. Most especially preferred Ar groups are those where the halogen substituent is fluorine.

As used herein, the following terms have the following meanings, unless expressly stated to the contrary.

The term "alkyl" refers to both straight- and branched-chain alkyl groups. The term "lower alkyl" refers to both straight- and branched-chain groups having a total of from 1 to 3 carbon atoms and includes primary and secondary alkyl groups. Typical lower alkyls include, for example, methyl, ethyl, n-propyl, isopropyl, and the like.

The term "halo" or "halogen" refers to the groups fluoro, chloro, bromo, and iodo.

The term "lower alkoxy" refers to the group OR' where R' is lower alkyl. Typical lower alkoxy groups include methoxy, ethoxy and the like.

The term "carbalkoxy" refers to the group

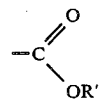

where R' is an alkyl group. The term "lower carbalkoxy" refers to carbalkoxy groups where R' is a lower alkyl group. Typical carbalkoxy groups include carbomethoxy, carboethoxy, and the like.

The terms "plant growth regulator" ("PGR") and "plant growth regulating" refer to compounds and/or their activities which alter growth or development of a plant as by a direct or indirect effect on natural phytohormone systems which may result in a beneficial increase or decrease in growth rate of the entire plant or a specific plant organ, or by helping a plant to adjust to stress, as by increased tolerance to drought, salt or wind. These growth regulating effects include, but are not limited to, increased branching, bud break at nodes which do not normally produce branches, increased or decreased set of flowers, reduction of stem height, preventing or retarding the growth of lateral buds, and promotion of the thinning out of superfluous fruits in various fruit trees.

DETAILED DESCRIPTION OF THE INVENTION

The compounds of the present invention may be prepared according to the following reaction sequence:

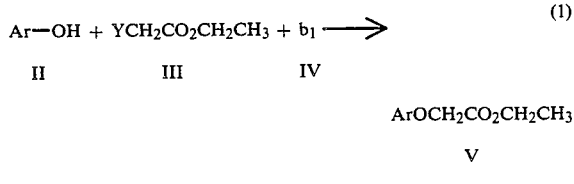

-continued $$V + b_2 \longrightarrow ArOCH_2CO_2H \quad (2)$$
$$\quad VI \quad\quad VII$$

$$VII + SOCl_2 \longrightarrow ArOCH_2\overset{O}{\underset{}{C}}Cl \quad (3)$$
$$\quad VIII \quad\quad IX$$

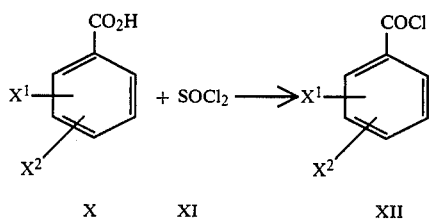 (4)

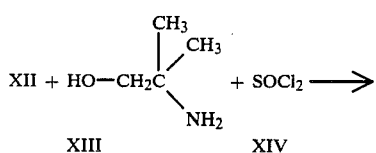 (5)

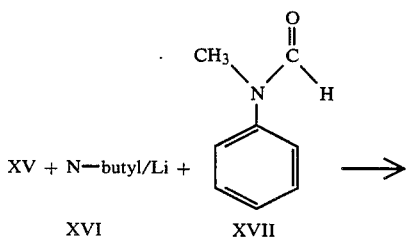 (6)

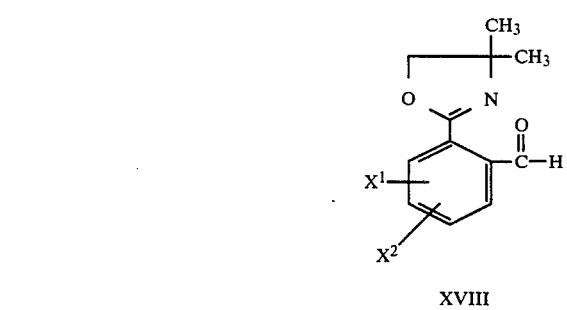 (7)

XVIII + Ac $\longrightarrow$
XIX

-continued

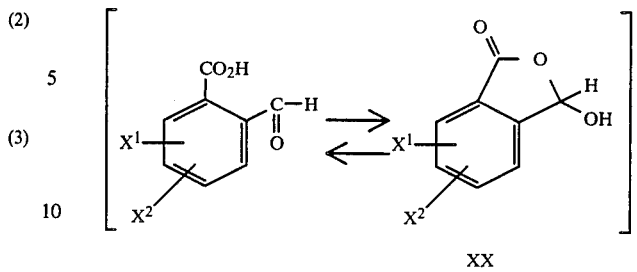

$$XX + (R^1)_2SO_4 + b_3 \longrightarrow \underset{XXIII}{\text{XXIII}} \quad (8)$$
$$\quad XXI \quad\quad XXII$$

$$XXIII + H_2NCH_2\overset{O}{\underset{}{C}}-R^2 + MgSO_4 \longrightarrow \quad (9)$$
$$\quad\quad XXIV \quad\quad\quad XXV$$

XXVI $$IX + XXVI + XXII \longrightarrow I \quad (10)$$

wherein $R^1$, $R^2$ and Ar are as previously defined in conjunction with formula I, Y is chlorine or bromine, Ac is an acid and $b_1$, $b_2$ and $b_3$ are bases.

Reaction (1) is conducted by combining approximately equimolar amounts of II, III and IV in solvent. Suitable bases, $b_1$, include inorganic bases such as potassium carbonate, and the like. Suitable solvents include inert organic solvents such as methyl ethyl ketone, acetone, toluene, other hydrocarbon solvents, and the like. The reaction is conducted at a temperature of about 20° to about 110° C., preferably from about 40° to about 80° C. and is generally complete within about 2 to about 10 hours. For convenience, the reaction may be carried out at ambient pressure. The product, V is isolated by conventional procedures such as filtration, evaporation under vacuum, and the like or alternatively after being filtered and stripped is used in reaction (2) without further isolation.

Some compounds V are commercially available such as those where Ar is unsubstituted phenyl, para-chlorophenyl 2,4-dichlorophenyl and 2,4,5-trichlorophenyl.

Reaction (2) is conducted by combining V and VI in solvent. It is preferred to use an excess of base, VI, preferably in the range of about 1.5 to about 3 equivalents VI per equivalent V. Suitable bases, $b_2$, include strong inorganic bases such as potassium hydroxide, sodium hydroxide, and the like. Suitable solvents include lower alcohols such as ethanol, and the like. The reaction is conducted at a temperature of about 20° to about 120° C., preferably from about 60° to about 90°

C., and is generally complete within 1 to about 4 hours. For convenience, the reaction may be carried out at ambient pressure. The product, VII, is isolated by conventional procedures such as stripping, extraction, and the like.

Reaction (3) is a conventional preparation of an acid chloride IX from the corresponding carboxylic acid, VII, using reagents well-known to those skilled in the art. For convenience, thionyl chloride, VIII, is used. Other suitable reagents include oxalyl chloride and the like. The reaction is conducted by combining approximately equimolar amounts of VII and VIII in solvent, although it is preferred to use a slight excess of VIII. The reaction is conducted at about 40° to about 150° C. preferably from about 80° to about 120° C., such as at reflux; and is generally complete within about ½ to about 3 hours. Suitable solvents include inert organic solvents such as toluene, benzene and the like. The product, IX, is isolated by conventional procedures such as stripping and the like, or alternatively, after removal of excess thionyl chloride, used in Reaction (10) without further isolation.

Certain acid chlorides, XII are commercially available; however, they may be prepared according to Reaction (4), which is also a conventional preparation of an acid chloride XII from the corresponding carboxylic acid X, using reagents well-known to those skilled in the art. For convenience, thionyl chloride, XI, is used. Other suitable reagents include oxalyl chloride and the like. The reaction is conducted by combining approximately equimolar amounts of X and XI in solvent, although it is preferred to use a slight excess of XI. The reaction is conducted at a temperature of about 20° C. to about 150° C., preferably from about 80° C. to about 120° C. or at reflux, and is generally complete within about ½ to about 3 hours. Suitable solvents include inert organic solvents such as toluene, benzene, methylene chloride and the like. The present, XII, is isolated by conventional procedures, such as stripping, distillation and the like; or, alternatively, after removal of excess thionyl chloride, used in Reaction (5) without further isolation.

Reaction (5) is conducted by combining XII, XIII and XIV in solvent. Although the reactants may be combined in a different order, it is preferred to slowly add XII in solvent to a cooled solution of XIII in solvent, followed by the addition of XIV. It may be preferable to stir the mixture of XII and XIII for a period of time before the addition of XIV in order to obtain a cleaner product. Suitable solvents include inert organic solvents such as methylene chloride, benzene and the like. Thionyl chloride, XIV, may be replaced by oxalyl chloride, carbonyldimidazole or other similar agents which activate the cyclization reaction. Excess XIII and XIV are used in relation to XII, on the order of about 1.1 to about 2.5 equivalents XIII per equivalent XII and about 1.1 to about 4 equivalents XIV per equivalent XII. The reaction is conducted at a temperature of about 0° C. to about 50° C., preferably from about 10° C. to about 25° C., and is generally complete within about 1 to about 4 hours. The product XV is isolated by conventional procedures, such as extraction, stripping, distillation, and the like.

Reaction (6) is conducted by combining XV, XVI and XVII in solvent. It is preferred to use an excess of XVI and XVII relative to XV, on the order of about 1.1 to about 2 equivalents XVI/XVII per equivalent XV. Although the addition may be done in different order, it is preferred to add XVI to XV in solvent, followed by XVII. It is preferable to keep the reaction mixture cooled to a temperature of about 0° C. during the additions, and to stir the reaction mixture for a period of time at about 0° C. between the additions to help ensure higher yields. The reaction is conducted at a temperature of about 0° C. to about 50° C., preferably from about 10° C. to about 25° C., and is generally complete within about 4 to about 24 hours. Suitable solvents include ethyl ether, tetrahydrofuran and the like. The product, XVIII is isolated by conventional procedures, such as extraction, distillation, and the like.

Reaction (7) is conducted by combining XVIII and XIX. Suitable acids Ac, XIX, include dilute mineral acids, such as dilute hydrochloric acid, sulfuric acid and the like. The reaction is conducted at a temperature of about 40° C. to about 100° C., preferably from about 60° C. to about 80° C., or at reflux; and is generally complete within about 4 to about 16 hours. The product XX, is isolated by conventional procedures, such as extraction, stripping and the like. Although initially the open ring form of the substituted carboxy benzaldehyde of XX is formed, it converts to the thermodynamically favored closed ring form.

Reaction (8) is conducted by combining XX, XXI and XXII in solvent. It is preferred to slowly and XXII to a stirred mixture of XX and XXI in solvent. It is preferred to use an excess of XXI and XXII in relation to XX, on the order of about 1 to about 3 moles of XXI per mole XX and about 1 to about 3 moles of XXII per mole XX. Suitable bases, $b_3$, include organic bases such as triethylamine, pyridine, and the like. The reaction is conducted at a temperature of about 30° to about 80° C., preferably about 40° to about 60° C. or at reflux, and is generally complete within about 1 to about 3 hours. Suitable solvents include inert organic solvents such as methylene chloride, benzene, and the like. The product, XXIII, is isolated by conventional procedures such as extraction, washing, drying, stripping, and the like.

Some compounds XXIII are commercially available, in such cases the commercial compound may be used directly to prepare intermediate XXVI according to Reaction (9).

Reaction (9) is conducted by adding XXIII to XXIV and XXV in solvent. Although approximately equimolar amounts of XXIII and XXIV may be used, it is preferred to use a very slight excess of XXIII. It is also preferred to add an approximately equimolar amount of anhydrous magnesium sulfate XXV to the XXIV-solvent mixture to remove water formed during the reaction. Alternatively, rather than using magnesium sulfate, the water formed during the reaction may be removed using other reagents or physical means well-known to those skilled in the art. The amino acid XXIV is normally used as a salt, such as a hydrochloride or tosylate, rather than as the free acid. The free acid is generated in situ by treatment with a base XXII such as triethylamine. It is preferred that an excess of XXII be used, about 1 to about 3 equivalents XXII per equivalent XXIV, preferably on the order of about 2 equivalents XXII per equivalent XXIV. The reaction is conducted at a temperature of about 0° to about 100° C., preferably from about 30° to about 50° C. or at reflux, and is generally complete within about 1 to about 3 hours. Suitable solvents include inert organic solvents such as methylene chloride, benzene, and the like. The product, XXVI, is isolated by conventional procedures such as filtration, concentration, and the like. It is preferred to use XXVI right away in Reaction (10).

Reaction (10) is conducted by combining IX, XXVI and XXII in solvent. Although approximately equimolar amounts of IX, XXVI and XXII may be used, it is preferred to use a slight excess of IX and XXII in relation to XXVI. The reaction is conducted at a temperature of about 0° to about 100° C., preferably from about 40° to about 80° C., and is generally complete within about 1 to about 3 hours. The product, I, is isolated by conventional procedures such as extraction, washing, concentration, trituration, and the like. Reaction (10) may produce a mixture of cis and trans isomers. The geometric isomers may be separated by conventional separation processes such as chromatography.

Reaction (10) may produce a mixture of geometric isomers. The conditions under which the reaction is conducted may influence which geometric isomer(s) is produced, and if a mixture is produced, the relative ratio of trans:cis. It is believed that factors such as the solvent used, the temperatures at which the addition of the reactants and the reaction itself are conducted and the order in which the reactants are combined may effect which isomer or isomers are formed. Thus, where n-hexane is the solvent used, a cis:trans isomer mixture is generally produced, whereas when the solvent is methylene chloride; benzene or toluene, formation of the trans isomer is favored. Conducting the reaction at a high temperature (e.g. reflux) especially at about 80° C., after the reactants have been combined generally favors formation of the trans isomer. Adding XXVI to IX in solvent followed by addition of XXII favors formation of the trans isomer. Thus, if XXVI is added to IX in solvent at 0° C., followed by addition of XXII and then heating the reaction mixture to reflux, predominately trans isomer is produced.

Utility

The compounds of the present invention are surprisingly active as plant growth regulators, and may effect plant growth in a variety of ways.

The plant growth regulating effects (PGR) of the present invention include herbistatic activity and thus, they may retard growth in plants such as grasses (requiring less frequent mowing) bedding plants and trees. The compounds may also be used as chemical pruning agents for plants such as fruit trees and bushy ornamentals. The compounds may be used as preconditioning agents for defoliation by promoting abscission and as agents for preventing late growth in crops such as cotton. Other PGR effects include increasing flowering and also effecting sex expression in flowering, for example increasing the number of female flowers and thus the number of fruits produced in plants such as cucumbers. Other PGR effects are evidenced in the biological testing data in Table II.

The compounds of the present invention are, in general, herbicidal and plant-growth regulating in post emergent applications. As noted above, the compounds are particularly effective as post-emergent plant-growth-regulators.

The compounds, when applied to the soil surrounding growing plants in such an amount that the compounds will not kill beneficial plants, show efficient plant growth regulating or retarding effects.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert a growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agent. Natural clays, either absorptive, such as attapulgite, or relatively non-absorptive, such as china clays, diatomaceous earth, synthetic fine silica, calcium silicate and other inert solid carriers of the kind conventionally employed in powdered growth-regulating compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

The amount of compound or composition administered will vary with the particular plant part or plant growth medium which is to be contacted, the general location of application—i.e., sheltered areas such as greenhouses, as compared to exposed areas such as fields—as well as the desired type of control. For plant growth regulating or retarding activity, it is essential to apply the compounds at a concentration not so high as to kill the plants. Therefore, the application rates for plant growth regulating or retarding activity will generally vary from 0.1 to 5 kg/ha, and preferably from 0.1 to 3 kg/ha.

A further understanding of my invention may be found in the following non-limiting examples.

EXAMPLES

EXAMPLE 1

Preparation of Ethyl para-fluorophenoxyacetate

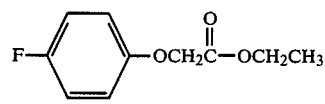

A mixture of 13.8 g (0.1 mole) potassium carbonate, 11.3 g (0.01 mole) 4-fluorophenol and 13.0 ml (19.6 g [0.11 mole]) ethyl bromoacetate in 100 ml methyl ethyl ketone were stirred overnight at room temperature and then heated at reflux for 5 hours. After the reaction mixture cooled to room temperature, it was filtered. The filtrate was concentrated to remove solvent. The concentrate was used as a whole without further isolation in Example 2.

EXAMPLE 2

Preparation of Para-fluorophenoxyacetic acid

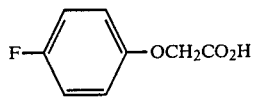

A mixture of ethyl para-fluorophenoxyacetate, the product of Example 1, (approximately 22.0 g (0.1 mole) and 20.0 g (0.3 mole) potassium hydroxide in 100 ml absolute ethanol was heated at reflux for three hours, cooled to room temperature and then stripped. The residue was taken up in 300 ml water. The aqueous solution was washed with 200 ml ether, acidified to give a pH of about 1 with concentrated hydrochloric acid and extracted a second time with ether. The second ethereal extract was washed with 200 ml water, dried with anhydrous magnesium sulfate and then concentrated to give 16.4 g of the product.

EXAMPLE 3

Preparation of Para-fluorophenoxyacetyl chloride

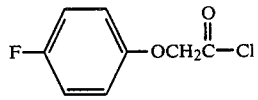

Into a 100 ml round bottom flask equipped with a magnetic stirrer, reflux condenser equipped with a connector to a 50% sodium hydroxide trap, 6.81 g (0.040 mole) para-fluorophenoxyacetic acid (the product of Example 2), 2.96 ml (0.044 mole) thionyl chloride, and about 40 ml toluene were placed. The reaction mixture was stirred at reflux for two hours, allowed to cool to room temperature, and then concentrated to give 7.2 g of the product, a brown liquid.

EXAMPLE 4

Preparation of 2-(4'-Fluorophenyl),4,4-dimethyl,5-oxazole

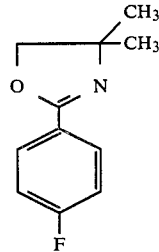

A mixture of 15.8 g [11.8 ml (0.1 mole)] p-fluorobenzoyl chloride in 25 ml methylene chloride was added dropwise to a cooled (to about 0° C.) solution of 19.61 g [21.0 ml (0.22 mole)] 2-amino-2-methyl-1-propanol in 40 ml methylene chloride. The resulting mixture was stirred at room temperature for 2.5 hours, filtered to remove solids and evaporated. Then 40.2 g [24.6 and (0.34 mole)] thionyl chloride was added dropwise. The reaction mixture was stirred about one-half hour and then poured into about 50 ml ethyl ether. The mixture was cooled in an ice bath; the pH was neutralized using 20% sodium hydroxide. The mixture was extracted with ether, dried over magnesium sulfate and evaporated to give about 19 g of the above-identified product, as a yellow oil which was then distilled under vacuum.

EXAMPLE 5

Preparation of 2-(2'-Formyl,4'-fluorophenyl),4,4-dimethyl,5-oxazole

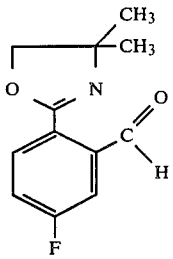

To a (stirred) mixture of 14.2 g (0.073 mole) 2-(4'-fluorophenyl),4,4-dimethyl,5-oxazole (the product of Example 4) in about 200 ml ethyl ether which had been cooled to about 0° C. in an ice/acetone bath, 35.3 ml (0.088 mole) 2.5M n-butyl lithium was added dropwise. The resulting mixture was stirred at about 0° C. for four hours, then, 11.9 g [10.9 ml (0.088 mole)] n-methylformanilide was added quickly. The reaction mixture was stirred over the weekend at room temperature. The reaction mixture was poured into water (about 100 ml) and then extracted with ethyl ether. The ether layer was washed with a sodium chloride solution, dried and evaporated to give a oily product. The oil was distilled at low pressure to give the 5.2 g of above-identified product as a yellow oil.

EXAMPLE 6

Preparation of 2-Carboxy-5-fluorobenzaldehyde

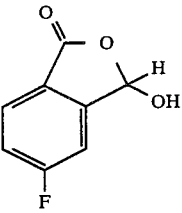

A stirred mixture of about 5.2 g 2-(2'-formyl,4'-fluorophenyl),4,4-dimethyl,5-oxazole (the product of Example 5) and hydrochloric acid (24.8 ml concentrated hydrochloric acid diluted to 100 ml with water was heated to almost reflux and maintained at that temperature overnight. The reaction mixture was cooled; ethyl ether was added. The resulting mixture was stirred. The layers were separated. The ether layer was dried and evaporated to give 3.5 g of the above-identified product, as a yellow solid.

EXAMPLE 7

Preparation of 2-Carbomethoxy-5-fluorobenzaldehyde

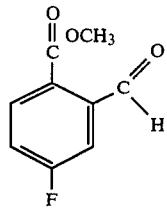

A stirred mixture of 3.4 g (0.02 mole) 2-carboxy-5-fluorobenzaldehyde (the product of Example 6) and 5.0 g [3.75 ml (0.04 mole)] dimethyl sulfate in methylene chloride was heated to reflux. The heating mantle was removed; and triethylamine, 4.15 g [5.7 ml (0.04 mole)] was added dropwise at a rate which maintained a brisk reflux. After the addition was complete, the reaction mixture was allowed to cool and was stirred at room temperature over the weekend. The reaction mixture was poured into water; the layers were separated. The methylene chloride layer was washed with a sodium bicarbonate solution, dried and evaporated to give 2.5 g of the above-identified product as a yellow oil.

EXAMPLE 8

Preparation of Ethyl(N-2-carbomethoxy-5-fluorobenzylidenyl)glycine

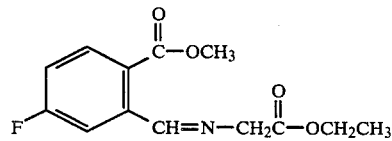

(a) Glycine ethyl ester hydrochloride 2.0 g (0.014 moles) was added to 3.2 g of 50% sodium hydroxide in methylene chloride. The mixture was stirred at room temperature for 15 minutes. The liquid was decanted, dried and evaporated to give the glycine ethyl ester.

(b) To a stirred mixture of 2.6 g (0.014 mole) 2-carbomethoxy-5-fluoro-benzaldehyde (the product of Example 7) and 6.7 g (0.056 mole) magnesium sulfate in methylene chloride, 1.47 g (0.014 mole) glycine ethyl ester was added dropwise. The reaction mixture was stirred overnight, then filtered and evaporated to give 3.5 g of the above-identified product as a yellow oil.

EXAMPLE 9

Preparation of 1-Carboethoxymethyl-3-para-chlorophenoxy-4-(2'-carbomethoxy-5'-fluorophenyl)-azet-2-one

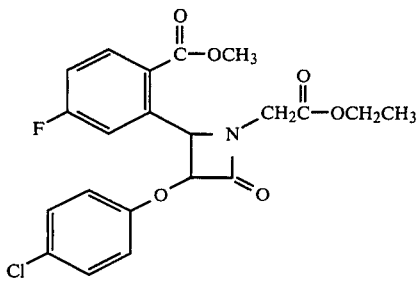

To a mixtures of 3.5 g (0.013 mole) ethyl (N-2-carbomethoxy-5-fluorobenzylidenyl)glycine (the product of Example 8) in 25 ml toluene which had been cooled to about 0° C., 2.7 g (0.013 mole) p-chlorophenylacetyl chloride was added dropwise; the temperature was maintained below 5° C. during the addition. The reaction mixture was stirred at about 0° C. for one hour. Then, 1.46 g [2.0 ml (0.014 mole)] triethylamine was added dropwise. The reaction mixture was heated to 70° C. for two hours, then cooled to room temperature, and diluted with water. The layers were separated. The organic layer was washed with 1N hydrochloric acid, 1N sodium hydroxide, and water; dried and evaporated. The oily residue was chromatographed using high pressure liquid chromatography, eluting with 3:1 hexane/ethyl acetate to give 2.0 g of the above-identified product as white crystals.

Elemental analysis for $C_{21}H_{19}NO_6FCl$ showed: calculated %C 57.9, %H 4.4, and %N 3.2; found %C 58.71, %H 4.5, and %N 3.75.

EXAMPLE 10

Preparation of 1-Carboethoxymethyl-3-para-fluorophenoxy-4-(2-carbomethoxy-5-methoxyphenyl)-acet-2-one

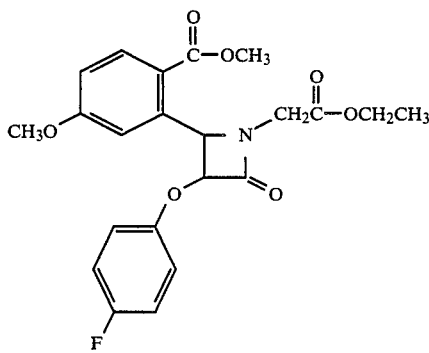

To a mixture of 3.7 g (0.015 mole) ethyl(N-2-carbomethoxy-5-methoxybenzylidenyl)glycine in 25 ml toluene cooled to about 0° C., 2.9 g (0.015 mole) p-fluorophenoxyacetyl chloride was added dropwise, while maintaining the temperature below 5° C. during the addition. The reaction mixture was stirred at about 0° C. for one hour, then triethylamine, 1.7 g (2.4 ml [0.017 mole)] was added dropwise. The reaction mixture was heated to 70° C. for two hours and then cooled to room temperature. The reaction mixture was diluted with water; the layers were separated. The organic layer was washed with 1N hydrochloric acid, 1N sodium hydroxide, the water; dried and evaporated to give 5.2 g of crude product, as a brown oil. The oil was chromatographed using HPLC, eluting with 3:1 hexane/ethylacetate to give the above-identified product as a yellow oil which solidified to give a yellow solid; melting point 78°-82° C.

Elemental analysis for $C_{22}H_{22}NO_7F$ showed: calculated %C 61.2, %H 5.1, and %N 3.2; found %C 63.05, %H 5.5, and %N 2.9.

Compounds which were made in accordance with Examples 1 to 10 using the appropriate starting materials are found in Table I.

In addition, by following the methods outlined in the Detailed Description of the Invention and disclosed in Examples 1 to 10 and using the appropriate starting materials and reagents, the following compounds are made:

1-Carboethoxymethyl-3-meta-methylphenoxy-4-(2'-carbomethoxy-5'-fluorophenyl)-azet-2-one;
1-Carboethoxymethyl-3-para-chlorophenoxy-4-(2'-carbomethoxy-5'-methylphenyl-azet-2-one;
1-Carboethoxymethyl-3-para-fluorophenoxy-4-(2'-carbomethoxy-5'-methylphenyl)-azet-2-one;
1-Carboethoxymethyl-3-(2',4'-dichlorophenoxy)-4-(2'-carbomethoxy-5'-fluorophenyl)-azet-2-one;
1-Carboethoxymethyl-3-meta-trifluoromethyl-4-(2'-carbomethoxy-5'-methoxyphenyl)-azet-2-one;
1-Carboethoxymethyl-3-(2'-methyl-4'-chlorophenyl)-4-(2'-carbomethoxy-5'-chlorophenyl)-azet-2-one;
1-Carboethoxymethyl-3-ortho-fluorophenoxy-4-(2'-carbomethoxy-5'-fluorophenyl)-azet-2-one;
1-Carbobenzyloxymethyl-3-para-fluorophenoxy-4-(2'-carboethoxy-5'-fluorophenyl-azet-2-one;
1-Carbobenzyloxymethyl-3-para-chlorophenoxy-4-(2'-carbomethoxy-5'-fluorophenyl)-azet-2-one;
1-Carbobenzyloxymethyl-3-para-fluorophenoxy-4-(2'-carbomethoxy-5'-chlorophenyl)-azet-2-one;
1-Carbobenzyloxymethyl-3-para-chlorophenoxy-4-(2'-carbomethoxy-5'-chlorophenyl)-azet-2-one;
1-Carbobenzyloxymethyl-3-para-fluorophenoxy-4-(2'-carbomethoxy-5'-methoxyphenyl)-azet-2-one; and
1-Carbobenzyloxymethyl-3-para-chlorophenoxy-4-(2'-carbomethoxy-5'-methoxyphenyl)-azet-2-one.

EXAMPLE A

Axillary Bud Inhibition Foliar Spray

The compounds of this invention were tested to determine their effect on axillary bud growth of Pinto Beans.

Pinto Bean plants, one pot per test compound (one plant per pot) were sprayed with an acetone-water carrier solution which contained a small amount of non-ionic emulsifier with a concentration of 200 ppm (or 625 ppm where noted) of test compound. A pot sprayed with the carrier solution without test compound was used as a check. One pot was sprayed with 100 ppm a-naphthyleneacetic acid as a standard. After spraying the solution was allowed to dry on the plant leaves; the plants were then transferred to a greenhouse maintained at 70°-80° F. and the plants were randomized.

The plants were read 12 days after treatment. Bud growth at the axil of the monofoliate leaf was read and expressed as % inhibition of axillary growth as compared to the untreated check topped above the monofoliate leaves. Results are given in Table II.

EXAMPLE B

Germination and Seedling Development Test

The compounds of this invention were tested to determine their effect on seed germination, seedling shoot and root development in two types of plant, mung beans and barnyard grass.

Seed pouches containing mung bean and barnyard grass seeds were treated with 15 ml of a solution containing 30 ppm (or 40 ppm where noted) of test compound in a water-acetone carrier formulation which contained a small amount of non-ionic emulsifier. A seed pouch treated with carrier formulation without test compound was used as a check. The seed pouches were then held under about 125-150 foot-candles of light for 24 hours per day for 7 days at room temperature.

Root length was measured for each species and expressed as % root inhibition as compared to the check. Results are given in Table II.

EXAMPLE C

Ethylene Evolution Test

The compounds of this invention were tested to determine their effect on ethylene evolution in plant tissue. Ethylene gas is a natural plant growth regulator which is produced by the plant when a change in growth or development occurs. Active levels of ethylene production from the leaf disc explant system may indicate wounding or damage to the plant tissue, a change in the enzyme or hormonal balance within the leaf disc, the onset of senescence of the leaf, or an increase in the metabolic rate of the tissue.

Vials each with two leaf discs cut from the monofoliate leaf of the pinto bean were treated with one ml of a $10^{-5}$ b-benzylaminopurine solution (BAP) and one ml of a 80 ppm (or 100 ppm or 250 ppm where noted) acetonewater solution of test compound which contained a small amount of non-ionic emulsifier. After treatment, the vials were capped and the time of capping noted. The vials were then incubated for 18 hours at room temperature in diffuse light. Vials containing one ml of BAP and one ml of 2% aqueous acetone were used as checks.

After incubation, one ml of gas mixture is removed from the upper portion of the vial and tested with a gas chromatograph. The data is recorded as % of reference where reference is 5 ppm ethylene in nitrogen gas. Results are given in Table II.

EXAMPLE D

Cotton Defoliation, Desiccation and Regrowth Inhibition

The compounds of this invention were tested to determine their effect on defoliation, desiccation and regrowth of cotton.

Cotton plants 4 to 5 weeks old having 4 true leaves above the cotyledonary leaves from which growth beyond the second true leaf had been removed not longer than 24 hours before treatment were used as test plants. The plants are treated by spraying with a 2000 ppm solution of test compound in an acetone-water carrier formulation which contained a small amount of non-ionic emulsifier. A plant sprayed with carrier formulation without test compound was used as the untreated check. An hour after spraying, the plants were transferred to a greenhouse maintained at about 85° F. (±5° F.) where they were allowed to incubate for 13 to 18 days before evaluation.

Defoliation or desiccation of each of the four leaves on each plant was evaluated, each leaf being 25% of the total. The combined defoliation/desiccation percentages cannot exceed 100%, since a leaf which both abscises and desiccates is noted only as "Defoliation".

Regrowth was noted as % inhibition of axillary bud growth as compared to the untreated check.

TABLE I

Compounds of the formula:

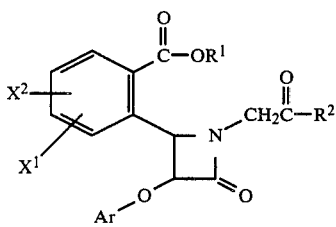

| Compound | Ar | R¹ | R² | X¹ | X² |
|---|---|---|---|---|---|
| 1 45000 | 4-F-C₆H₄ | —CH₃ | —OCH₂CH₃ | 5-OCH₃ | H |
| 2 45101 | 4-F-C₆H₄ | —CH₃ | —OCH₂CH₃ | 4-OCH₃ | H |
| 3 45002 | 4-Cl-C₆H₄ | —CH₃ | —OCH₂CH₃ | 5-OCH₃ | H |
| 4 45001 | 4-F-C₆H₄ | —CH₃ | —OCH₂CH₃ | 5-Cl | H |
| 5 45100 | 4-Cl-C₆H₄ | —CH₃ | —OCH₂CH₃ | 5-F | H |
| 6 45099 | 4-Cl-C₆H₄ | —CH₃ | —OCH₂CH₃ | 5-Cl | H |

TABLE II

| Compound | ABI | GSD-MB | GSD-BG | EE | C DEF. | C DES. | CRInh. |
|---|---|---|---|---|---|---|---|
| 1 45000 | 98 | 92 | 92 | 102 | 0 | 0 | 89 |
| 2 45101 | 0 | 92 | 50 | 146 | 0 | 0 | 48 |
| 3 45002 | 100 | 100 | 100 | 274 | 0 | 0 | 100 |
| 4 45001 | 98 | 92 | 92 | 196 | 0 | 0 | 98 |
| 5 45100 | 0 | 83 | 83 | 24 | 0 | 0 | 93 |
| 6 45099 | 0 | 83 | 83 | 0 | 0 | 0 | 93 |

ABI = Axillary Bud Growth Inhibition
GSD-MB = Germination & Seed Development - Mung Bean
GSD-BG = Germination & Seed Development Barnyard grass
EE = Ethylene Evolution
C DEF = Cotton Defoliation
C DES = Cotton Desiccation
CRInh = Cotton Regrowth Inhibition

What is claimed is:

1. A compound of the formula:

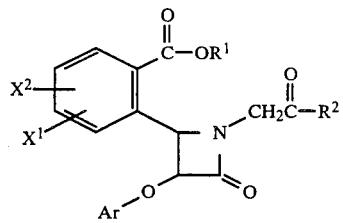

wherein R¹ is lower alkyl or benzyl; R² is lower alkoxy, benzyloxy or the group

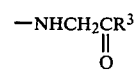

where R³ is lower alkoxy; Ar is phenyl or phenyl substituted with 1 to 3 substituents independently selected from halogen, trihalomethyl, nitro, phenyl, lower alkoxy and lower alkyl; and X¹ and X² are independently hydrogen, halogen, lower alkoxy, or lower alkyl, or X¹ and X² taken together form an aromatic ring fused with the phenyl ring, provided that both X¹ and X² are not hydrogen.

2. A compound according to claim 1 wherein the compound is the trans isomer.

3. A compound according to claim 1 wherein Ar is phenyl optionally substituted with up to two halogen atoms.

4. A compound according to claim 3 wherein Ar is phenyl substituted with one halogen atom.

5. A compound according to claim 4 wherein Ar is the group

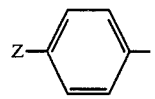

wherein Z is halogen.

6. A compound according to claim 5 wherein X¹ is halogen or lower alkoxy and X² is hydrogen.

7. A compound according to claim 6 wherein X¹ is 5-substituted.

8. A compound according to claim 7 wherein R² is lower alkoxy.

9. A compound according to claim 8 wherein X¹ is chloro, fluoro or methoxy.

10. A compound according to claim 9 wherein R¹ is methyl or ethyl and R² is methoxy or ethoxy.

11. A compound according to claim 10 wherein Z is chloro or fluoro.

12. A compound according to claim 11 wherein $R^1$ is methyl and $R^2$ is ethoxy.

13. A compound according to claim 12 wherein $X^1$ is 5-methoxy and Z is chloro.

14. A compound according to claim 13 wherein the compound is the trans isomer.

15. A compound according to claim 12 wherein $X^1$ is 5-methoxy and Z is fluoro.

16. A compound according to claim 15 wherein the compound is the trans isomer.

17. A compound according to claim 12 wherein $X^1$ is 5-chloro and Z is fluoro.

18. A compound according to claim 17 wherein the compound is the trans isomer.

19. A compound according to claim 1 wherein $R^2$ is lower alkoxy or benzyloxy.

20. A compound according to claim 19 wherein Ar is phenyl optionally substituted with up to two halogen atoms.

21. A compound according to claim 20 wherein $X^1$ is lower alkoxy or halogen and $X^2$ is hydrogen.

22. A plant growth regulating composition comprising a biologically inert carrier and a plant growth regulating effective amount of a compound of claim 1.

23. A plant growth regulating composition comprising a biologically inert carrier and a plant growth regulating effective amount of a compound of claim 2.

24. A plant growth regulating composition comprising a biologically inert carrier and a plant growth regulating effective amount of a compound of claim 7.

25. A plant growth regulating composition comprising a biologically inert carrier and a plant growth regulating effective amount of a compound of claim 13.

26. A plant growth regulating composition comprising a biologically inert carrier and a plant growth regulating effective amount of a compound of claim 15.

27. A plant growth regulating composition comprising a biologically inert carrier and a plant growth regulating effective amount of a compound of claim 17.

28. A method for regulating the growth of vegetation which comprises applying to said vegetation or its habitat a plant growth regulating effective amount of a compound of claim 1.

29. A method for regulating the growth of vegetation which comprises applying to said vegetation or its habitat a plant growth regulating effective amount of a compound of claim 2.

30. A method for regulating the growth of vegetation which comprises applying to said vegetation or its habitat a plant growth regulating effective amount of a compound of claim 7.

31. A method for regulating the growth of vegetation which comprises applying to said vegetation or its habitat a plant growth regulating effective amount of a compound of claim 13.

32. A method for regulating the growth of vegetation which comprises applying to said vegetation or its habitat a plant growth regulating effective amount of a compound of claim 15.

33. A method for regulating the growth of vegetation which comprises applying to said vegetation or its habitat a plant growth regulating effective amount of a compound of claim 17.

* * * * *